(12) United States Patent
Galea et al.

(10) Patent No.: US 11,181,132 B2
(45) Date of Patent: Nov. 23, 2021

(54) APPARATUS AND METHOD FOR CONTROLLING FLUID FLOW

(71) Applicant: Vivonics, Inc., Bedford, MA (US)

(72) Inventors: Anna Galea, Stow, MA (US); Joseph Beuford Parse, Stow, MA (US); Kylie Stengel, Allston, MA (US); Kristen LeRoy, Waltham, MA (US); Minh Duong, Worcester, MA (US); Samuel Harrington Warner, Brighton, MA (US); Andrew Evan Kamholz, Brookline, MA (US); Brandon Johnson, Somerville, MA (US)

(73) Assignee: Vivonics, Inc., Bedford, MA (US)

( * ) Notice: Subject to any disclaimer, the term of this patent is extended or adjusted under 35 U.S.C. 154(b) by 100 days.

(21) Appl. No.: 16/398,070

(22) Filed: Apr. 29, 2019

(65) Prior Publication Data

US 2019/0331145 A1    Oct. 31, 2019

Related U.S. Application Data

(60) Provisional application No. 62/664,494, filed on Apr. 30, 2018.

(51) Int. Cl.
*F15B 21/06* (2006.01)
*F15D 1/06* (2006.01)
(Continued)

(52) U.S. Cl.
CPC ............... *F15D 1/06* (2013.01); *A61M 1/32* (2013.01); *F15D 1/025* (2013.01); *A61M 2206/11* (2013.01); *A61M 2206/16* (2013.01)

(58) Field of Classification Search
CPC .. F15D 1/06; F15D 1/025; A61M 1/32; A61M 1/36; A61M 1/14; A61M 2206/11;
(Continued)

(56) References Cited

U.S. PATENT DOCUMENTS 5,961,832 A     10/1999  Shaw et al.
6,217,539 B1 *  4/2001   Goldau ............... A61M 1/1615
                                                       604/4.01
(Continued)

FOREIGN PATENT DOCUMENTS

EP       0 790 849 A1    8/1997
WO       WO-96/12541 A1  5/1996

OTHER PUBLICATIONS

International Search Report and Written Opinion of the International Searching Authority dated Sep. 26, 2019 in International Application No. PCT/US2019/029736, 19 pages.
(Continued)

*Primary Examiner* — Minh Q Le
(74) *Attorney, Agent, or Firm* — Morse, Barnes-Brown & Pendleton, P.C.; Stanley F. Chalvire, Esq.

(57) ABSTRACT

Apparatuses for flowing multiple fluids in a single channel while substantially maintaining fluid separation are disclosed. In one configuration, the apparatus includes a first internal surface portion with an affinity to a first fluid and a second internal surface portion with an affinity to a second fluid. In another configuration, the apparatus includes a first fluid channel portion, a second fluid channel portion wrapped helically around the first fluid channel portion, and an opening therebetween. Also disclosed is an apparatus for maintaining substantially even fluid flow in fluid pathways having a first flow resistor portion, a second flow resistor portion, and a fluid channel therebetween.

10 Claims, 17 Drawing Sheets

(51) Int. Cl.
  *A61M 1/32* (2006.01)
  *F15D 1/02* (2006.01)
(58) Field of Classification Search
  CPC ........... A61M 2206/16; A61M 2205/12; B01L 2200/0636; B01L 2300/165; B01L 2300/0816; B01L 3/502776
  USPC ......................................................... 137/806
  See application file for complete search history.

(56) References Cited

U.S. PATENT DOCUMENTS

| | | | | |
|---|---|---|---|---|
| 6,432,630 | B1* | 8/2002 | Blankenstein | B01D 57/02 435/4 |
| 6,541,213 | B1* | 4/2003 | Weigl | B01F 5/0403 210/198.2 |
| 7,276,170 | B2* | 10/2007 | Oakey | B01D 57/02 204/451 |
| 2001/0035350 | A1* | 11/2001 | Seki | G01N 15/1404 204/412 |
| 2001/0048637 | A1* | 12/2001 | Weigl | B01F 5/0647 366/341 |
| 2001/0055546 | A1* | 12/2001 | Weigl | B01F 13/0059 422/400 |
| 2003/0034306 | A1* | 2/2003 | Schulte | F16K 99/0001 210/650 |
| 2004/0219078 | A1* | 11/2004 | Kitamori | B01F 13/0062 422/504 |
| 2005/0061962 | A1* | 3/2005 | Mueth | A61M 1/36 250/251 |
| 2005/0121604 | A1* | 6/2005 | Mueth | B03C 1/28 250/251 |
| 2005/0266582 | A1 | 12/2005 | Modlin et al. | |
| 2006/0042950 | A1* | 3/2006 | Sarrut | B01L 3/502776 204/600 |
| 2006/0076295 | A1* | 4/2006 | Leonard | B01D 61/28 210/645 |
| 2008/0056953 | A1* | 3/2008 | Yamada | B01L 3/502776 422/504 |
| 2008/0131323 | A1* | 6/2008 | Kuczenski | B01L 3/502769 422/82.13 |
| 2009/0078614 | A1* | 3/2009 | Varghese | B03C 1/0332 209/39 |
| 2009/0220932 | A1* | 9/2009 | Ingber | G01N 15/1484 435/2 |
| 2010/0047761 | A1* | 2/2010 | MacDonald | C12M 47/04 435/2 |
| 2012/0061304 | A1 | 3/2012 | Leonard et al. | |

OTHER PUBLICATIONS

Partial International Search Report dated Jul. 30, 2019 received in corresponding International Application No. PCT/US2019/029736, 10 pages.
International Preliminary Report on Patentability in International Application No. PCT/US2019/029736 dated Nov. 12, 2020, 11 pages.

* cited by examiner

APPARATUS AND METHOD FOR CONTROLLING FLUID FLOW

CROSS-REFERENCE TO RELATED APPLICATION

This application claims priority to U.S. Provisional Patent Application No. 62/664,494, filed Apr. 30, 2018, which application is incorporated herein by reference in its entirety.

FIELD

The present disclosure relates generally to apparatuses and methods for flowing multiple fluids in a single channel while substantially maintaining fluid separation and also to apparatuses and methods for maintaining substantially even fluid flow in fluid pathways.

BACKGROUND

In certain applications, it is desirable to have two or more fluids flow in a single channel without substantial intermixture of the fluids. One such application involves flowing both blood and a second fluid in a single channel to facilitate molecular transport between the blood and the second fluid. Blood is a non-Newtonian fluid that includes blood plasma and blood cells suspended within the plasma. Red blood cells (RBCs) have a shape as biconcave discs and can deform and tumble during blood flow. Because RBCs have a momentum separate from a momentum of the surrounding fluid, RBCs have a tendency to cross streamlines or fluid layers during blood flow. Additionally, during flow, RBCs tend to tumble away from areas of high shear in the fluid.

Previous approaches to fluid flow of blood and a second fluid have involved using a physical membrane to ensure fluid separation (i.e., prevent fluid intermixture) between blood and a second fluid. However, such approaches render it difficult or impossible to facilitate molecular transport between the blood and the second fluid. Also, such approaches can lead to biofouling of the physical membrane and thrombogenesis in the blood caused by contact between the blood and the physical membrane.

Consequently, there is a need for apparatuses and methods for flowing multiple fluids, including blood, in a single channel to facilitate molecular transport between the multiple fluids while maintaining fluid separation and substantially avoiding coagulation in the blood. Additionally, there is a need for such apparatuses and methods to be sanitary.

To increase throughput, it can be desirable to provide a number of single channels extending in parallel. To supply fluid to such single channels, it can be efficient to feed the fluid into an input and spread the fluid through separate input channels to each of the parallel channels. However, it is difficult to maintain substantially even fluid flow in the parallel channels. Generally, in fluid systems, uneven levels of flow in multiple parallel channels result, due to different levels of fluid resistance present in each parallel channel. A channel having a lesser least fluid resistance will enable a greater flow rate, and, conversely, a fluid channel having a greater fluid resistance will have a lower flow rate.

Previous approaches generally require the use of flow resistors in the form of a narrow point (also known as "pinch points") in a fluid channel which create a greater pressure drop across the fluid channel. The greater pressure drop across the fluid channel causes small fluctuations in fluid flow to have a smaller effect on flow in the channel than in the absence of the flow resistors. However, pinch points are not feasible for use in a medical device (e.g., a device used for blood flow) because the pinch points create regions of high shear rates, which cause hemolysis (i.e., the rupture or destruction of RBCs in the blood).

Consequently, there is a need for apparatuses and methods for ensuring balanced and even flow of a fluid flowing through multiple parallel channels simultaneously without creating regions of high shear rates in the fluid flow.

SUMMARY

At least one aspect of the present disclosure relates to an exemplary embodiment of an apparatus for flowing multiple fluids in a single channel while substantially maintaining fluid separation. The apparatus includes a fluid channel configured to receive a first fluid and a second fluid. At least a portion of the fluid channel has a first internal surface portion and a second internal surface portion. The first internal surface portion is configured to have an affinity to the first fluid and the second internal surface portion is configured to have an affinity to the second fluid, and the first internal surface portion and the second internal surface portion have different fluid affinities. The at least a portion of the fluid channel, including the first internal surface portion and the second internal surface portion, is configured to maintain substantially stable flow of the first fluid and the second fluid within the at least a portion of the fluid channel.

Another aspect of the present disclosure relates to an exemplary embodiment of an apparatus for flowing multiple fluids in a single channel while substantially maintaining fluid separation. The apparatus includes a fluid channel including a first fluid channel portion configured to receive a first fluid, a second fluid channel portion configured to wrap helically around the first fluid channel portion and configured to receive a second fluid, and an opening configured to allow for fluid contact between the first fluid flowing through the first fluid channel portion and the second fluid flowing through the second fluid channel portion.

Another aspect of the present disclosure relates to an exemplary embodiment of an apparatus for maintaining substantially even fluid flow in fluid pathways. The apparatus includes a first fluid input; a first set of fluid pathways in fluid communication with the first fluid input, wherein each fluid pathway of the first set of fluid pathways includes at least a first flow resistor portion configured to cause substantially even fluid flow across the first set of fluid pathways; and a fluid channel disposed downstream of the first flow resistor portion.

DETAILED DESCRIPTION

Figure 1:
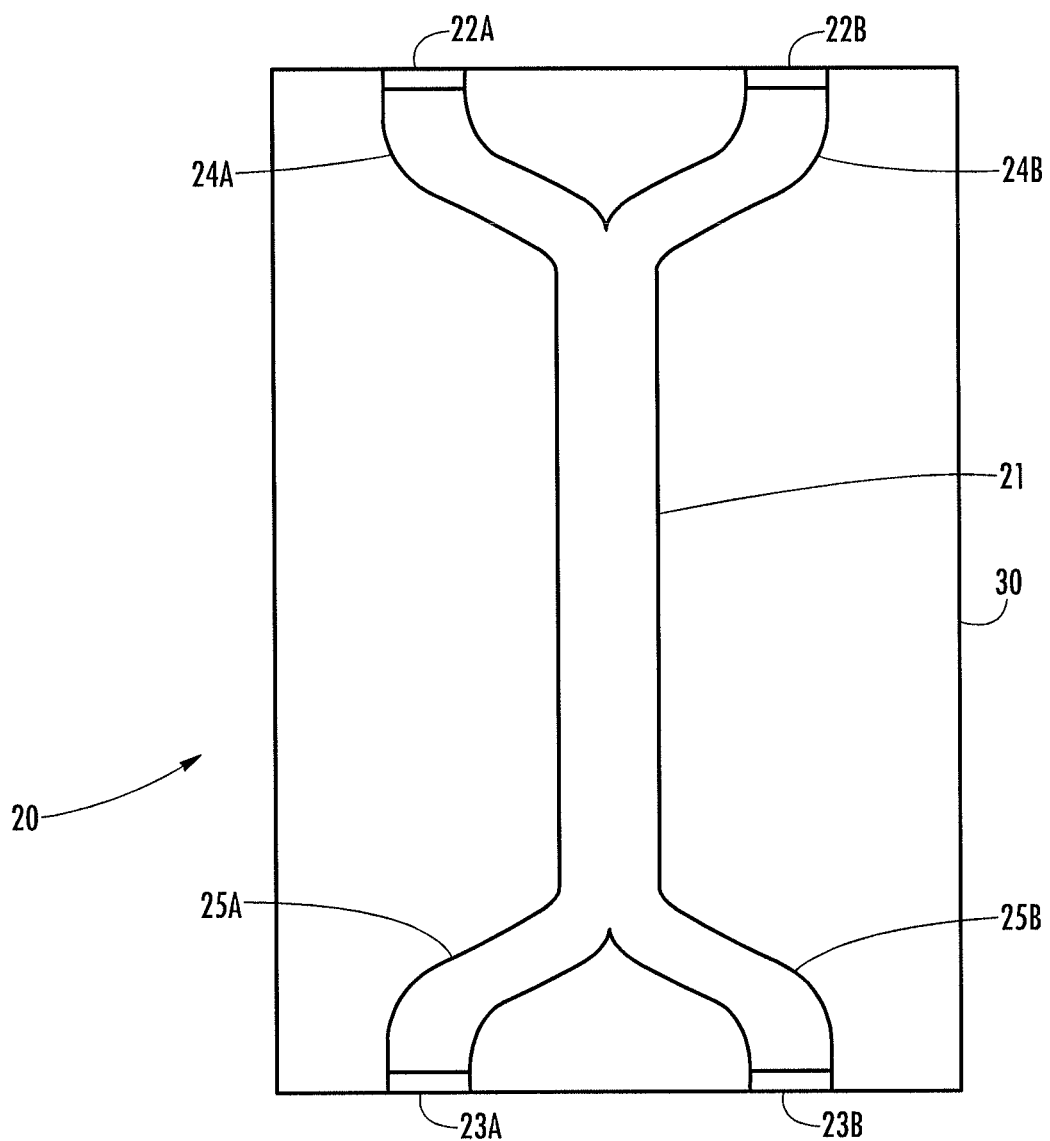
FIG. 1 is a front view of an embodiment of an apparatus configured to allow multiple fluids to flow in a fluid channel while substantially maintaining fluid separation.

Referring generally to the FIGURES, apparatuses are shown and described for flowing multiple fluids in a single fluid channel to facilitate molecular transport between the fluids while substantially maintaining fluid separation. Also, an apparatus is shown and described that equilibrates fluid flow in multiple channels.

I. First Embodiment of an Apparatus for Flowing Multiple Fluids in a Single Channel A. Overview Disclosed herein are embodiments of an apparatus for flowing multiple fluids, preferably immiscible, in a single channel while substantially maintaining fluid separation. The multiple immiscible fluids may be, for example, blood and a second fluid (e.g., perflourodecalin), but may be other fluids such as oil and water. An apparatus for flowing blood and second fluid is significant because of a need for molecular transport between the blood and the second fluid (e.g., transport of oxygen molecules into the blood and carbon dioxide molecules out of the blood) in a sanitary environment (e.g., avoiding contaminating the blood or biofouling a fluid membrane).

Stable or laminar flow refers to fluid flow in which layers of fluid within a flow slip smoothly over one another without causing disruptions between the fluid layers. In other words, laminar flow is characterized as orderly and predictable fluid flow. In contrast, turbulent flow refers to fluid flow in which layers of fluid disrupt each other in a manner which renders the flow difficult to describe precisely because such flow is characterized as irregular, random, and chaotic. In the apparatus disclosed herein, preferably fluid flow within the apparatus is characterized by a Reynold's number of about 10.

Such fluid flow can be obtained, for example, by unique millifluidic (or mesofluidic) configurations. Millifluidics (or mesofluidics) involves manipulating and controlling fluids, usually in the range of milliliters ($10^{-3}$), in networks of channels with cross-sectional dimensions typically of about 0.75 to 1.5 millimeters. Because of the small scale in millifluidics, the dominant force acting within the small channels is surface tension. In such cases, the volumetric flow rates and the relative viscosity of immiscible fluids flowing in the same channel determine the total amount of a cross section of the channel that each fluid will occupy within the channel. If an interface between the multiple fluids does not reach across the channel (i.e., from one side of the channel to a second, opposite side of the channel), stable fluid flow can be maintained in the channel because fluid separation will be substantially maintained due to the fluid interface acting as a pseudo-membrane. The pseudo-membrane stores energy associated with a surface area of the pseudo-membrane and creates a pressure differential between the multiple fluids related to a curvature of the pseudo-membrane. The pressure differential causes the interface to bow in and out away from an edge of the channel that subtends the interface.

It has been determined that stable fluid flow in a single channel can be obtained by configuring internal surfaces to have different affinities to different, immiscible fluids. Accordingly, a first immiscible fluid flows along a first internal surface or surfaces to which the first fluid has an affinity and a second immiscible fluid flows along a second internal surface or surfaces to which the second fluid has an affinity.

B. Housing

FIG. 1 shows a front view of an apparatus 20 configured to allow the flow of multiple fluids in the same fluid channel 21. The apparatus 20 is particularly useful for flowing multiple fluids in cases in which one of the fluids is blood. Apparatus 20 includes a housing 30 that can support the fluid channel 21 configured to facilitate two fluids flowing through the channel.

The housing 30 also can support structure for supplying fluids to the fluid channel 21. For example, a first fluid input 22A and a second fluid input 22B can be in fluid communication with an input channel 24A and an input channel 24B, respectively. In turn, the input channel 24A and the input channel 24B are in fluid communication with the fluid channel 21.

Figure 2:
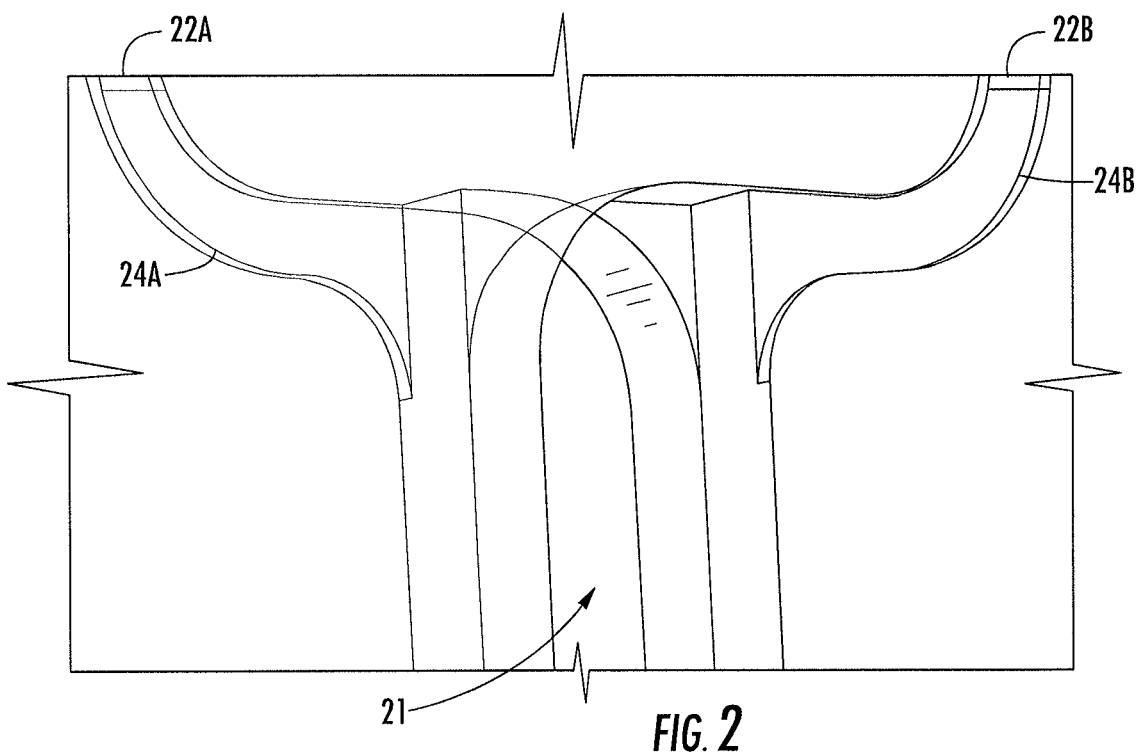
FIG. 2 is a perspective view of an embodiment of a fluid input portion of the fluid channel in the apparatus shown in FIG. 1.

Each of inputs 22A and 22B can be configured, by conventional means, for connection with a respective fluid source (not shown) (e.g., an IV bag, etc.), such that fluid inputs 22A and 22B receive a first fluid and a second fluid, respectively, from the fluid sources. As shown in FIG. 2, the first and second fluids each flow through respective input channels 24A and 24B into fluid channel 21.

The housing 30 also can support structure for receiving fluids from the fluid channel 21. For example, an output channel 25A and an output channel 25B are in fluid communication with the fluid channel 21. In turn, the output channel 25A and the output channel 25B are in fluid communication with a first fluid output 23A and a second fluid output 23B.

Figure 3:
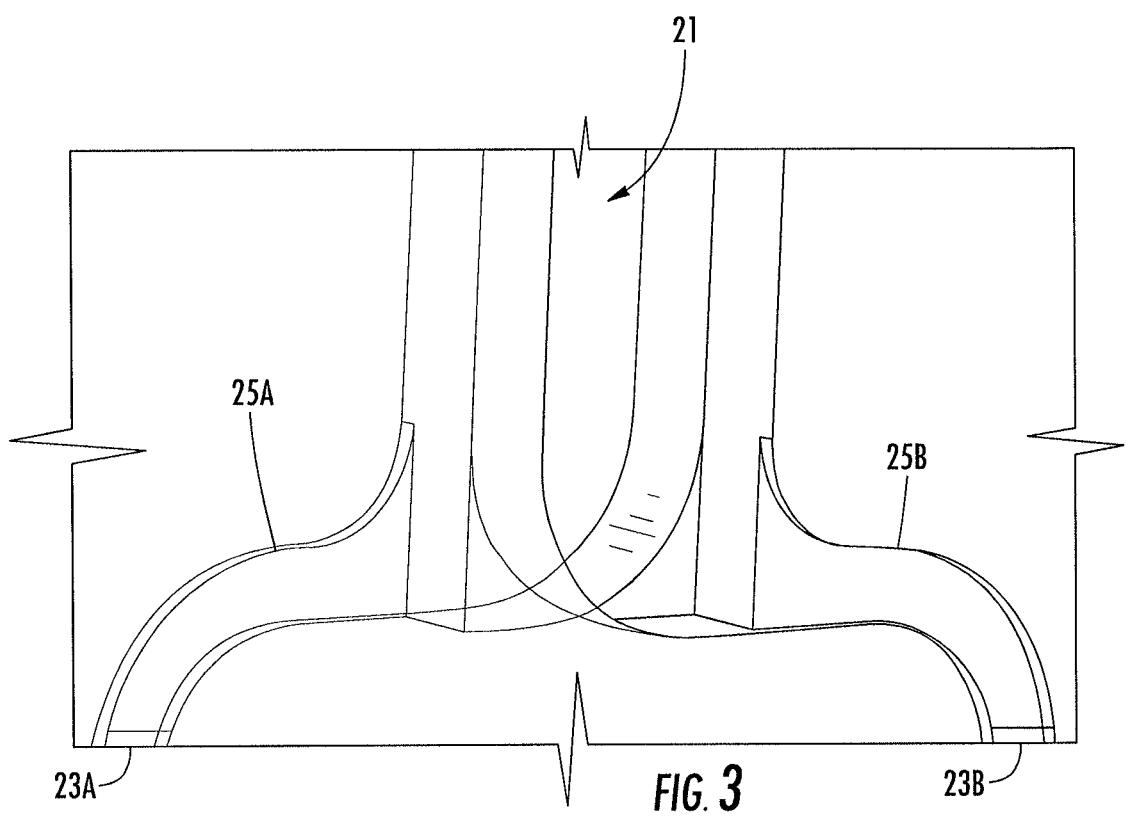
FIG. 3 is a perspective view of a fluid output portion of the fluid channel shown in FIG. 1.

As shown in FIG. 3, for example, output channels 25A and 25B receive respective fluids from the fluid channel 21. The output channels 25A and 25B provide the respective fluids to the first fluid output 23A and the second fluid output 23B, respectively. Fluid outputs 23A and 23B are configured to exit a fluid flowing out of the apparatus. The fluid outputs 23A and 23B can be configured, by conventional means, for connection with further tubing or other receptacles for the fluids.

Preferably, the housing 30 supports the fluid channel 21 such that fluid can be pumped to flow through the fluid channel such that the system (and specifically the fluid flow) is unaffected by gravity.

C. Fluid Channel

The fluid channel 21 is configured to allow flow of multiple fluids (e.g., the first and second fluids) while substantially maintaining fluid separation. Thus, molecular transport can be facilitated between the two fluids without fluid intermixture occurring.

The fluid channel 21 can be formed in a variety of configurations. For example, it can be a flexible or rigid channel. Additionally, it can have a variety of cross-sectional shapes, but a rectangular cross-sectional shape with four sides is preferred. The fluid channel 21 can be formed of any suitable material for transporting biomaterials.

Figure 4A:
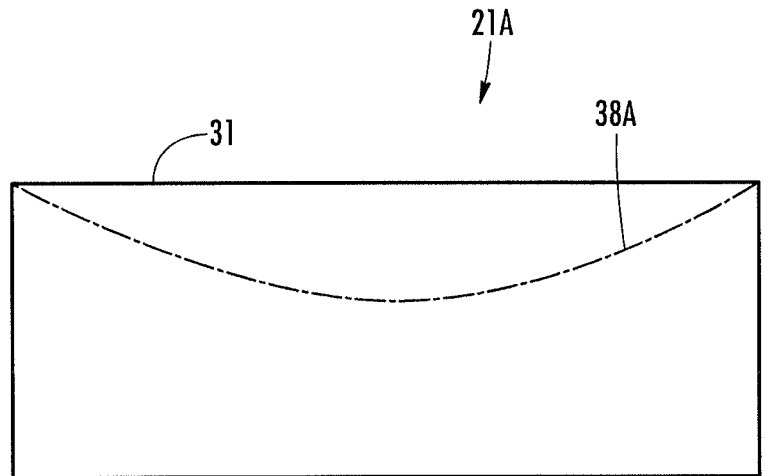
FIG. 4(a)-(c) show a cross-sectional view of an embodiment of the fluid channel shown in FIG. 1.
Figure 4B:
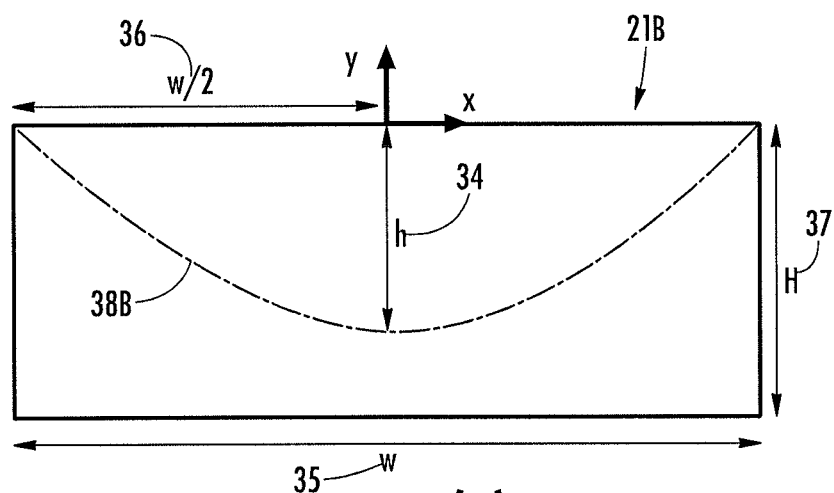
Figure 4C:
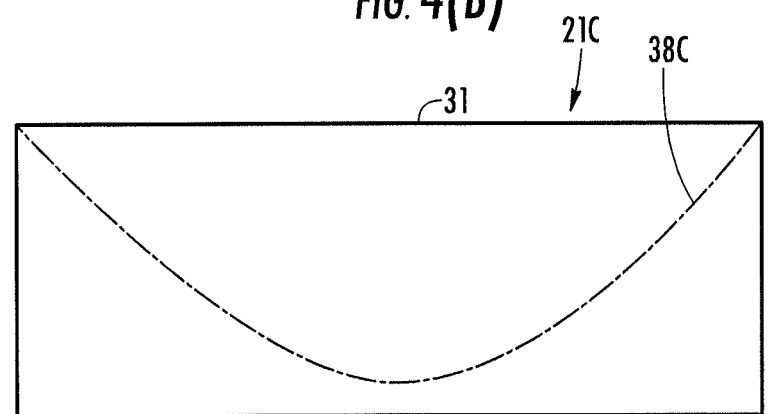

FIGS. 4(*a*)-(*c*) show a cross-sectional view of an embodiment of the fluid channel 21. For example, as shown in FIG. 4(*a*)-(*c*), fluid channel 21 has a rectangular cross section. Fluid channel 21 has a width w 35 and a half-width w/2 36, as well as a height H 37. Further, fluid channel 21 has at least one first internal surface 31 and at least one second internal surface 32.

The at least one first internal surface 31 has an affinity to a first fluid, and the at least one second internal surface 32 has an affinity to a second fluid. The affinity of the internal surfaces 32 can be established in a variety of ways. For example, the affinity can be established by the material of the corresponding portion of the fluid channel 21. For example, a hydrophilic surface could be made of hydrogels, polyamides, or hydroxylated polyurethanes. As another example, a hydrophobic surface could be made of polytetrafluoroethylene or polymethylene. Alternatively, the affinity can be established by a treatment, such as a coating, applied to the interior of the fluid channel 21. Such treatments include plasma or corona treatments or coating a surface with hydrogels, polyamides, or hydroxylated polyurethanes (to create a hydrophilic surface) or coating a surface with polytetrafluoroethylene or polymethylene (to create a hydrophobic surface. For example, the affinity of each internal surface can be established by applying a first coating on the at least one first internal surface and applying a second coating to the at least one second internal surface. As a more specific example, the above substances can be applied in any suitable order, with appropriate masking (e.g., apply or coat a first coating on the first internal surface, mask the first coating, and apply or coat a second coating on the second internal surface).

As one example of the affinities of the surfaces for the fluids, the at least one first internal surface 31 can be configured to be one of oleophobic and hydrophobic and the at least one second internal surface 32 can be configured to be the other of oleophobic and hydrophobic. In a further example, the at least one first internal surface 31 can be configured to be one of hydrophilic and hydrophobic and the second internal surface can be configured to be the other of hydrophilic and hydrophobic 32. For example, for hydrophilicity a contact angle with water of no more than 50 degrees is preferred, and for hydrophobicity a contact angle with water of more than 110 degrees is preferred.

When multiple immiscible fluids flow in fluid channel 21, a fluid interface 38 is created by a first fluid and a second fluid. Depending on parameters, such as the configuration of the fluid channel 21, the flow rates, and the fluids used, the fluid interface may occur at different locations within the fluid channel 21. For example, the parameters may cause the fluid interface 38A to exist at the location in the fluid channel 21A shown in FIG. 4(*a*). As another example, the parameters can cause the fluid interface 38B to exist at the location in the fluid channel 21B shown in FIG. 4(*b*). As a still further example, the parameters can cause the fluid interface 38C to exist at the location in the fluid channel 21C shown in FIG. 4(*c*).

The shape of fluid interface 38 approximates a segment of a circle. However, using a parabolic shape to estimate an extent to which the first fluid extends into the second fluid will overestimate the height of the fluid interface because the height of the segment from the chord that subtends the circle is less than the height of the parabola. Accordingly, such an approach will provide an additional margin to prevent the fluid interface from reaching across the fluid channel.

The shape of a parabola is generally defined by relationship (1): $y=f(x)$, where the function $f(x)$ is generally of the form given such that relationship (2) defines the shape of a parabola:

$y=Cx^2-h$, with respect to the dimensions in FIG. 2. Using known coordinates ($y=0$, $x=w/2$) in this relationship (2), relationship (3) gives the value for $C=4h/w^2$.

As a result, the shape of the interface (as estimated by a parabolic shape is described by relationship (4):

$$y=h(4x^2/w^2-1)$$

Thus, an area of the first fluid that lies within the parabola (that is, in the area of fluid channel 21 that is above fluid interface 38 and below internal surface portion 31) is given by relationship (5):

$$A_1=\tfrac{2}{3}hw$$

The second fluid therefore occupies the remaining space in fluid channel 21 and this area is described by relationship (6):

$$A_2=Hw-\tfrac{2}{3}hw$$

Assuming equal volumetric flow rates (a volumetric flow rate of the first fluid is equal to a volumetric flow rate of the second fluid), the ratio of areas occupied by the first fluid and the second fluid in fluid channel 21 is determined by a viscosity of the first fluid and a viscosity of the second fluid, with a relatively more viscous fluid taking up a proportionally greater amount of area. This can be expressed by relationship (7):

$$A_1/u_1=A_2/u_2$$

Using relationship (7) to relate relationship (5) to relationship (6) yields the following derivation for relationship (8):

$$\tfrac{2}{3}hw/u_1=Hw/u_2-\tfrac{2}{3}hw/u_2$$

and relationship (9):

$$h/u_1=3/2(H/u_2-\tfrac{2}{3}h/u_2)=3/2H/u_2-h/u_2$$

and relationship (10):

$$h(1/u_1+1/u_2)=3/2H/u_2$$

Solving for the height h 34 of the fluid interface yields relationship (11):

$$h = 3/2H \, u_1/(u_1+u_2)$$

Therefore, the height h 34 of the fluid interface is equal to the channel height H 37 when relationship (12) holds:

$$3/2u_1/(u_1+u_2)-1=0$$

Relationship (12) holds when relationship (13) is true: $u_1=2u_2$. In other words, the fluid interface 38 will reach from one side to an opposite side of the fluid channel 21 when a dynamic viscosity of the first fluid is equal to twice a dynamic viscosity of the second fluid.

Assuming, therefore that a volumetric flow rate of the first fluid is equal to a volumetric flow rate of the second fluid, the fluid interface will remain substantially stable (i.e., the fluid interface will not reach across the fluid channel) as long as a dynamic viscosity of the first fluid is less than twice a dynamic viscosity of the second fluid, that is, the relationship of the dynamic viscosities of the two fluids satisfies the condition of $u_1<2u_2$, where $u_1$ is the dynamic viscosity of the first fluid and $u_2$ is the dynamic viscosity of the second fluid.

Figure 5:
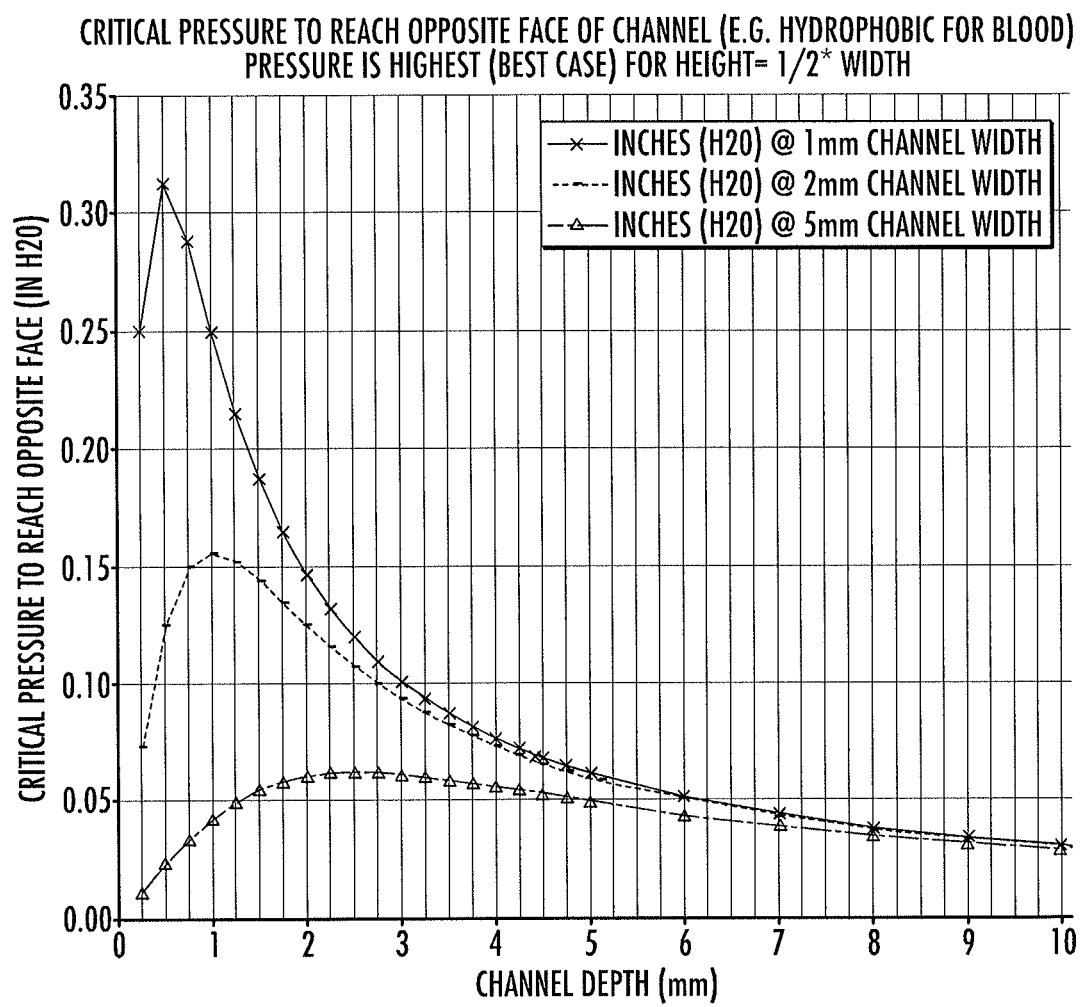
FIG. 5 is a graph illustrating calculations for the height and width of the fluid channel shown in FIG. 1.

FIG. 5 is a graph illustrating empirical results regarding a ratio of width 35 to height 37 for the fluid channel 20 for maintaining an ideal stability of the interface such that the interface remains within the edges of the channel and does not incur onto the opposite edge of the fluid channel. Empirically, substantial stability of the interface can be maintained if the width to height ratio is within a range of 1:2 to 10:1, inclusive. Preferably, the ratio is 3:2. More preferably, the ratio is 2:1, at which ratio the pressure differential at the fluid interface required to push the interface to the opposite edge is greatest.

Figure 6:
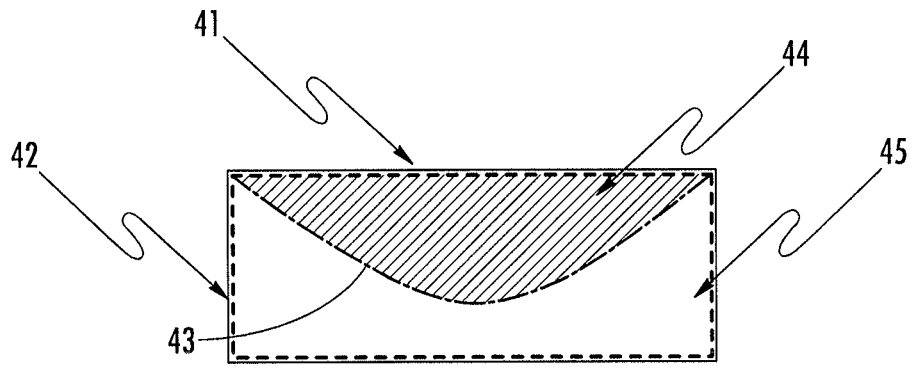
FIG. 6 is a cross-sectional view of an embodiment of the fluid channel shown in FIG. 1.
Figure 7:
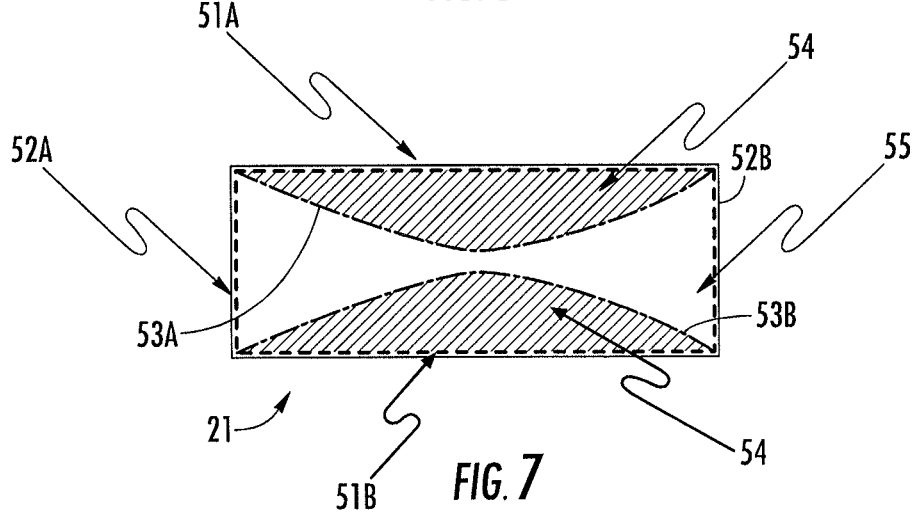
FIG. 7 is a cross-sectional view of an embodiment of the fluid channel shown in FIG. 1.
Figure 8:
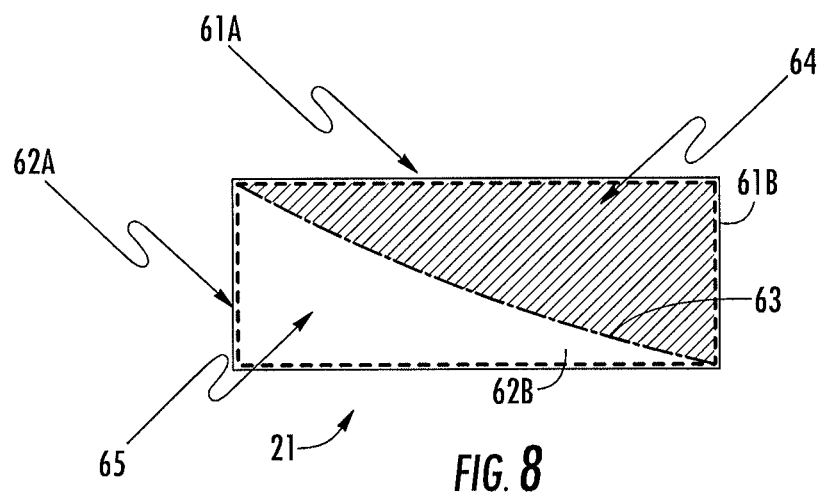
FIG. 8 is a cross-sectional view of an embodiment of the fluid channel shown in FIG. 1.

FIGS. 6-8 show three exemplary embodiments for fluid channel 21. In each of these embodiments, different internal surface portions of the fluid channel are each configured to have affinities to different fluids. A first internal surface portion has an affinity to a first fluid (e.g., an aqueous fluid) and a second internal surface portion has an affinity to a second fluid (e.g., an oleic fluid). In some embodiments, the first internal surface portion has an affinity to an aqueous fluid and the second internal surface portion has an affinity to an oleic fluid.

Because the first fluid and the second fluid are immiscible, the first internal surface portion and the second internal surface portion have different fluid affinities. Further, the first internal surface portion and the second internal surface portion are configured to substantially maintain stable fluid flow of the two immiscible fluids in the fluid channel.

According to the embodiment illustrated in FIG. 6, an internal surface 41 is configured to have an affinity to a first fluid 44. Internal surface or surfaces 42 are configured to have an affinity to a second fluid 45. When immiscible fluids 44 and 45 flow in fluid channel 21, the fluids form a fluid interface 43 which creates a pseudo-membrane.

According to the embodiment illustrated in FIG. 7, internal surfaces 51A and 51B of fluid channel 21 are configured to have an affinity to a first fluid 54. Internal surfaces 51A and 51B are opposite sides of fluid channel 21. Internal surfaces 52A and 52B of fluid channel 21 are configured to have an affinity to a second fluid 55, and internal surfaces 52A and 52B are the other of the opposite sides of channel 21. When immiscible fluids 54 and 55 flow in fluid channel 21, the fluids form fluid interfaces 53A and 53B, which create pseudo-membranes. The pseudo-membrane substantially maintains fluid separation because of the high forces due to a pressure differential existing along fluid interfaces 53A and 53B. As long as the fluid interfaces 53A and 53B do not meet, stable, separate fluid flow is substantially maintained in fluid channel 21.

According to the embodiment illustrated in FIG. 8, fluid channel 21 has internal surfaces 61A and 61B which are adjacent to each other and are configured to have an affinity to a first fluid 64. Additionally, fluid channel 21 has internal surfaces 62A and 62B which are adjacent to each other and are configured to have an affinity to a second fluid 65. When immiscible fluids 64 and 65 flow in fluid channel 21, the fluids form fluid interface 63, which creates a pseudo-membrane. The pseudo-membrane substantially maintains fluid separation because of the high forces due to a pressure differential existing along fluid interface 63. As long as fluid interface 63 does not extend to and touch either of internal surfaces 62A or 62B, stable, separate fluid flow is substantially maintained in fluid channel 21.

As described herein, embodiments can be constructed in which multiple fluids are flowed in a single channel 21, while substantially maintaining fluid separation. While it is desired to maintain 100% fluid separation, it is understood that sufficient fluid separation can be an amount of separation that may be less than 100% fluid separation, while still being acceptable commercially or for the particular application. In some embodiments, there can be at least 90% fluid separation. In some embodiments, there can be at least 95% fluid separation. In some embodiments, there can be at least 98% fluid separation. In some embodiments, there can be at least 99% fluid separation.

II. Second Embodiment of an Apparatus for Flowing Multiple Fluids in a Single Channel

A. Overview

Disclosed herein is an embodiment of an apparatus for flowing multiple fluids, preferably immiscible, in a single fluid channel while substantially maintaining fluid separation. The multiple immiscible fluids may be, for example, blood and a second fluid (e.g., perflourodecalin), but may be other fluids such as oil and water. An apparatus for flowing blood and the second fluid is significant because of a need for molecular transport between the blood and the second fluid (e.g., transport of oxygen molecules into the blood and carbon dioxide molecules out of the blood) in a sanitary environment (e.g., avoiding contaminating the blood or biofouling a fluid membrane).

Separate fluid flow of two immiscible fluids (one of which preferably is blood) can be maintained in a single fluid channel by configuring the physical structure of the fluid channel to take advantage of the unusual fluid characteristics of blood flow due to RBCs in the blood (e.g., the deformation and tumbling of RBCs during flow and the tumbling of RBCs away from regions of high shear). The fluid channel is configured to employ helical flow such that a first fluid flows in an inner, central straight path and a second fluid flows in an outer, helical path around the inner, central straight path. For example, the first fluid is blood and fluid separation between the blood and the second fluid is substantially maintained because RBCs in the blood will tend to tumble to the middle of the flow in the central, straight path. In a further example, the second fluid is blood and fluid separation between the blood and the first fluid is substantially maintained because a rotational flow of RBCs in the blood in the outer, helical path, will tend to tumble towards the outside of the outer flow path and away from the first fluid.

Such an apparatus can be useful for hemodialysis and blood oxygenation because of the need to prevent RBCs from intermixing with another fluid without using a physical membrane.

B. Housing

Figure 9:
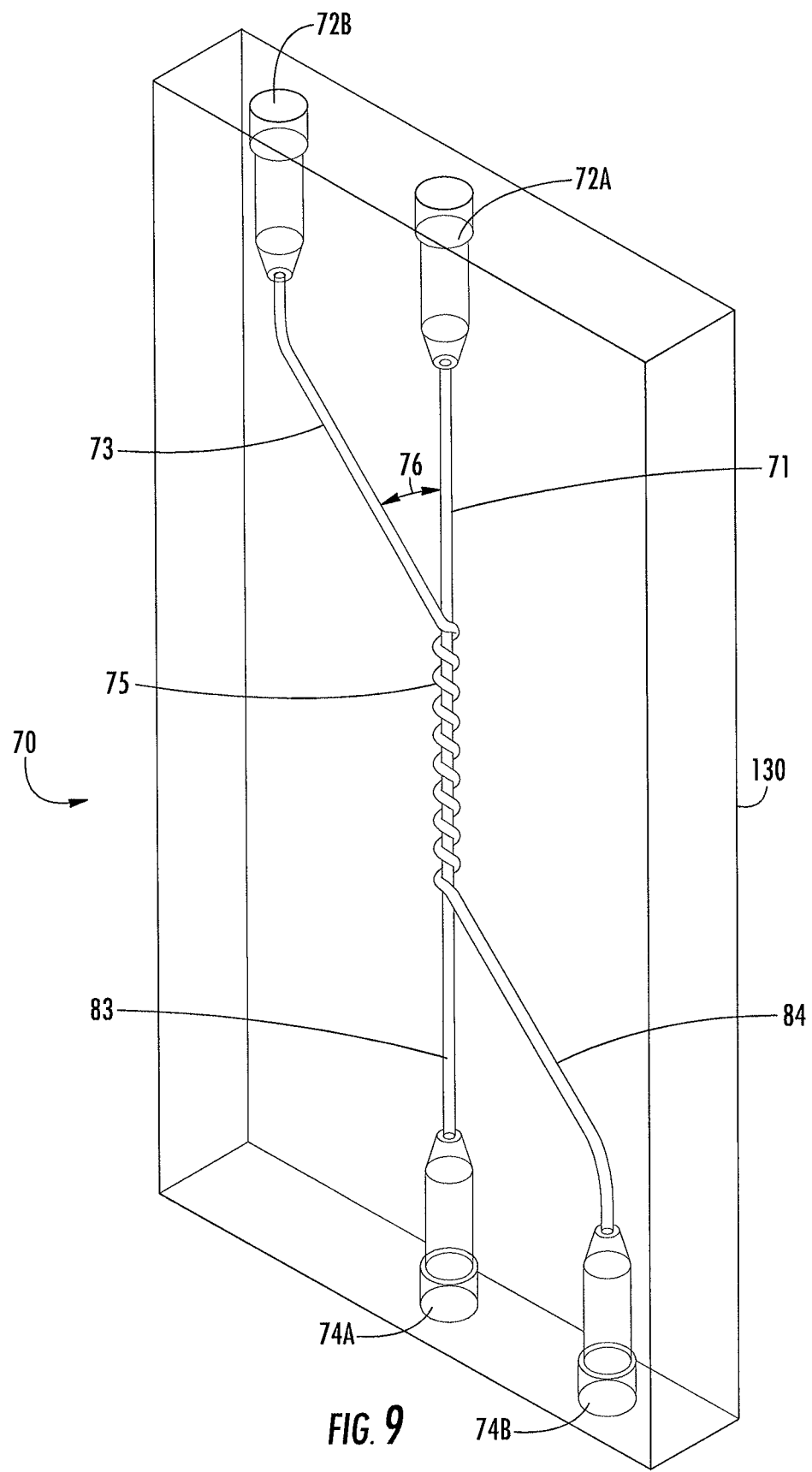
FIG. 9 is a perspective view of an embodiment of an apparatus configured to allow multiple fluids to flow in a fluid channel while substantially maintaining fluid separation.

FIG. 9 shows a perspective view of an apparatus 70 for flowing multiple fluids in a single fluid channel 75 while substantially maintaining fluid separation. The apparatus 70 is particularly useful for flowing multiple fluids in cases in which one of the fluids is blood. Apparatus 70 includes a housing 130 that can support the fluid channel 75 configured to facilitate two fluids flowing through the channel.

The housing 130 also can support structure for supplying fluids to the fluid channel 75. For example, a first fluid input 72A and a second fluid input 72B can be in fluid communication with an input channel 71 and an input channel 73, respectively. In turn, the input channel 71 and the input channel 73 are in fluid communication with the fluid channel 75.

Figure 10:
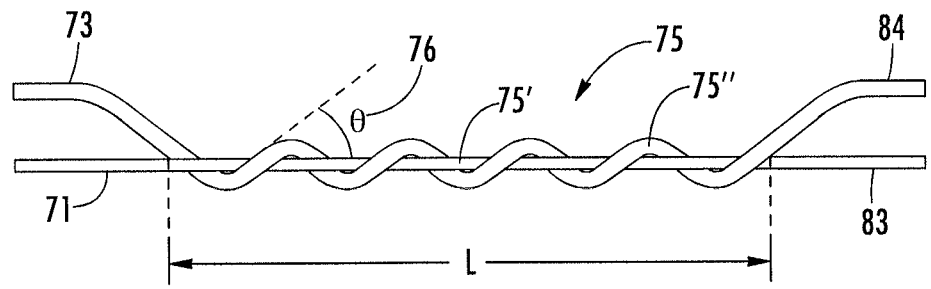
FIG. 10 is a front view of an embodiment of a portion of the fluid channel of the apparatus shown in FIG. 9.

Each of first and second fluid inputs 72A and 72B can be configured, by conventional means, for connection with a respective fluid source (not shown) (e.g., an IV bag, etc.), such that fluid inputs 72A and 72B receive a first fluid and a second fluid, respectively, from the fluid sources. As shown in FIG. 10, the first and second fluids each flow through respective input channels 71 and 73 into fluid channel 75.

The housing 130 also can support structure for receiving fluids from the fluid channel 75. For example, an output channel 83 and an output channel 84 are in fluid communication with the fluid channel 75. In turn, the output channel 83 and the output channel 84 are in fluid communication with a first fluid output 74A and a second fluid output 74B.

As shown in FIGS. 9 and 10, for example, output channels 83 and 84 receive respective fluids from the fluid channel 75. The output channels 83 and 84 provide the respective fluids to the first fluid output 74A and the second fluid output 74B, respectively. Fluid outputs 74A and 74B are configured to exit a fluid flowing out of the apparatus. The fluid outputs 74A and 74B can be configured, by conventional means, for connection with further tubing or other receptacles for the fluids.

Preferably, the housing 130 supports the fluid channel 75 such that fluid can be pumped to flow through the first channel such that the system (and specifically the fluid flow) is unaffected by gravity.

C. Fluid Channel

The fluid channel 75 is configured to allow flow of multiple fluids (e.g., the first and second fluids) while substantially maintaining fluid separation. Thus, molecular transport can be facilitated between the two fluids without fluid intermixture occurring. The fluid channel 75 can include a first fluid channel portion 75' and a second fluid channel portion 75".

1. First Fluid Channel Portion

FIG. 10 illustrates an exemplary embodiment of the first fluid channel portion 75' of the fluid channel 75. In a preferred embodiment, the first fluid channel portion 75' is a continuation or extension of the input channel 71 and the output channel 83 (e.g., having the same central axis and/or the same cross-sectional dimensions); however, the first fluid channel portion 75' has an opening 81 (shown in FIG. 11) that allows fluid communication with the second fluid channel portion 75".

Figure 11:
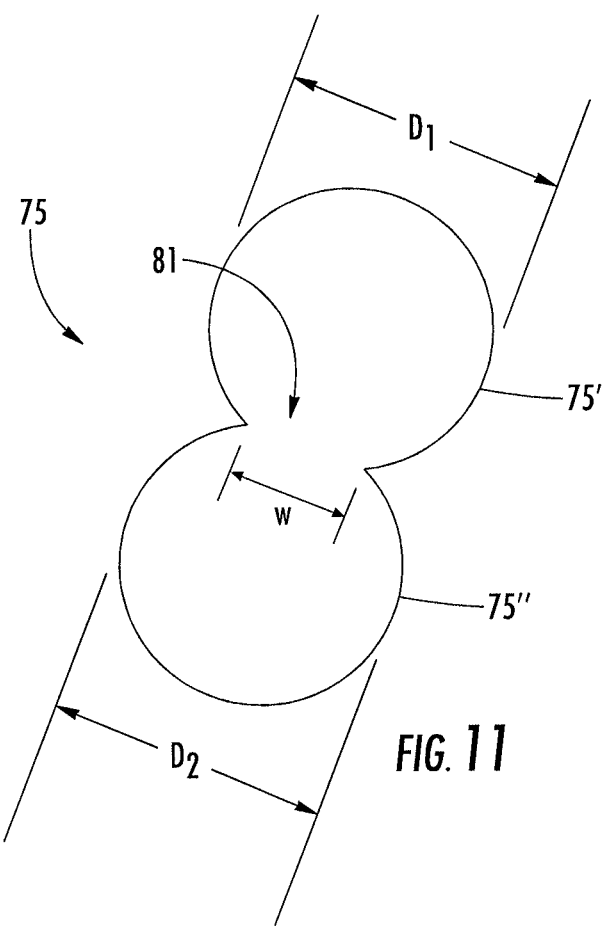
FIG. 11 is a cross-sectional view of the portion of the fluid channel shown in FIG. 10.

Preferably, the first fluid channel portion 75' is substantially straight. As shown in FIG. 11, the first fluid channel portion 75' preferably has a substantially circular cross section with a diameter $D_1$. The first fluid channel portion 75' may have any suitable cross-sectional shape or size configured to facilitate flow of a first fluid (e.g., blood or an oleic fluid) through the first fluid channel portion 75'.

The first fluid channel portion 75' is configured to receive a first fluid from the input channel 71. The first fluid channel portion 75' is configured such that a portion of the first fluid channel portion 75' is in fluid communication with the second fluid channel portion 75" through the opening 81. The first fluid channel portion 75' directs the first fluid to flow into the output channel 83 to exit the apparatus.

2. Second Fluid Channel Portion

FIG. 10 illustrates an exemplary embodiment of the second fluid channel portion 75" of the fluid channel 75. In a preferred embodiment, the second fluid channel portion 75" is a continuation or extension of the input channel 73 and the output channel 84 (e.g., having the same central axis and/or the same cross-sectional dimensions); however, the second fluid channel portion 75" has an opening 81 that allows fluid communication with the first fluid channel portion 75'.

As shown in FIG. 11, the second fluid channel portion 75" preferably has a substantially circular cross section with a diameter $D_2$. The second fluid channel portion 75" may have any suitable cross-sectional shape or size configured to facilitate flow of a second fluid (e.g., blood or an oleic fluid) through the second fluid channel portion 75". The size of the second fluid channel portion 75" in some embodiments is the same as the size of the first fluid channel portion 75', but they conceivably could be different in some embodiments.

The second fluid channel portion 75" is configured to receive a second fluid, which is different from the first fluid, from the input channel 73. The second fluid channel portion 75" is configured such that the opening 81 of the second fluid channel portion 75" is in fluid communication with the first fluid channel portion 75'. The second fluid channel 75" directs the second fluid to flow into the output channel 84 to exit the apparatus.

As shown in FIG. 10, the second fluid channel portion 75" preferably is configured to wrap helically around the first fluid channel portion 75' at an angle 76. The angle of the second fluid channel portion 75" relative to the first fluid channel portion 75' may be any suitable angular dimension.

3. Opening

As shown in FIG. 11, the opening 81 allows fluid communication between the first fluid flowing in the first fluid channel portion 75' and the second fluid flowing in the second fluid channel portion 75". Specifically, fluid communication occurs through the opening 81 along an edge of first fluid channel portion 75' and an edge of second fluid channel portion 75". The opening 81 has a width W, which has any suitable size such that molecular transport can occur between the first fluid and the second fluid while substantially maintaining fluid separation between the first and the second fluids. Preferably, the dimensions and configuration of the opening 81 allow for molecular transport between the first fluid and the second fluid.

With reference to FIG. 10, Table 1 reports exemplary dimensions for the first fluid channel portion and the second fluid channel portion according to this second embodiment. Length L is preferably less than 100 mm. Diameters $D_1$ and $D_2$ are preferably less than 1 mm, and angle 76 is preferably any suitable angle for the intended purpose.

TABLE 1

|  | Angle 76 | Diameter $D_1$ | Diameter $D_2$ | Length L | Width W |
|---|---|---|---|---|---|
| Design 1 | 45° | 0.6 mm | 0.6 mm | 50 mm | 0.4 mm |
| Design 2 | 30° | 0.4 mm | 0.6 mm | 50 mm | 0.25 mm |

As described herein, embodiments can be constructed in which multiple fluids are flowed in a single channel 75, while substantially maintaining fluid separation. While it is desired to maintain 100% fluid separation, it is understood that sufficient fluid separation can be an amount of separation that may be less than 100% fluid separation, while still being acceptable commercially or for the particular application.

III. Embodiment of an Apparatus for Maintaining Substantially Even Fluid Flow in Fluid Pathways A. Overview To increase throughput, it can be desirable to provide an apparatus having a number of fluid pathways that preferably each include, for example, the fluid channels 21 and 75 described above. To supply fluid to such fluid channels, it can be efficient to feed the fluid into an input and spread the fluid to each of the fluid channels via the separate fluid pathways.

To maintain substantially even fluid flow across the fluid pathways, an apparatus for equilibrating fluid flow is disclosed. Generally, in fluid systems, uneven levels of flow in parallel fluid pathways result due to different levels of fluid resistance present in each fluid pathway. A fluid pathway having a lesser fluid resistance will enable a greater flow rate, and, conversely, a fluid pathway having a greater fluid resistance will have a lower flow rate.

In the apparatus disclosed herein, flow resistor portions are provided in each of the fluid pathways. The flow resistor portions can equalize the levels of fluid resistance present in each fluid pathway, thereby maintaining substantially even fluid flow across the fluid pathways. For example the flow resistor portions can add a pressure drop to the fluid flow in each of the fluid pathways.

The apparatus may have more than one set of fluid pathways. An embodiment will be described having two sets of fluid pathways. The first set of fluid pathways will be described in detail, with it being understood that the second set of fluid pathways can be configured to have essentially the same structure. Alternatively, the second set of fluid pathways can be configured to have a different structure, as described in more detail below. Each set of fluid pathways can receive a respective fluid. For example, the first set of fluid pathways can receive a first fluid and the second set of fluid pathways may receive a second fluid. According to a preferred embodiment, the first fluid may be blood and the second fluid may be a perfluorocarbon. Each fluid pathway of the first set of fluid pathways may have a fluid channel that coincides with a corresponding fluid channel of a fluid pathway in the second set of fluid pathways to facilitate molecular transport between fluids in the first and second sets of fluid pathways.

B. Housing

Figure 12:
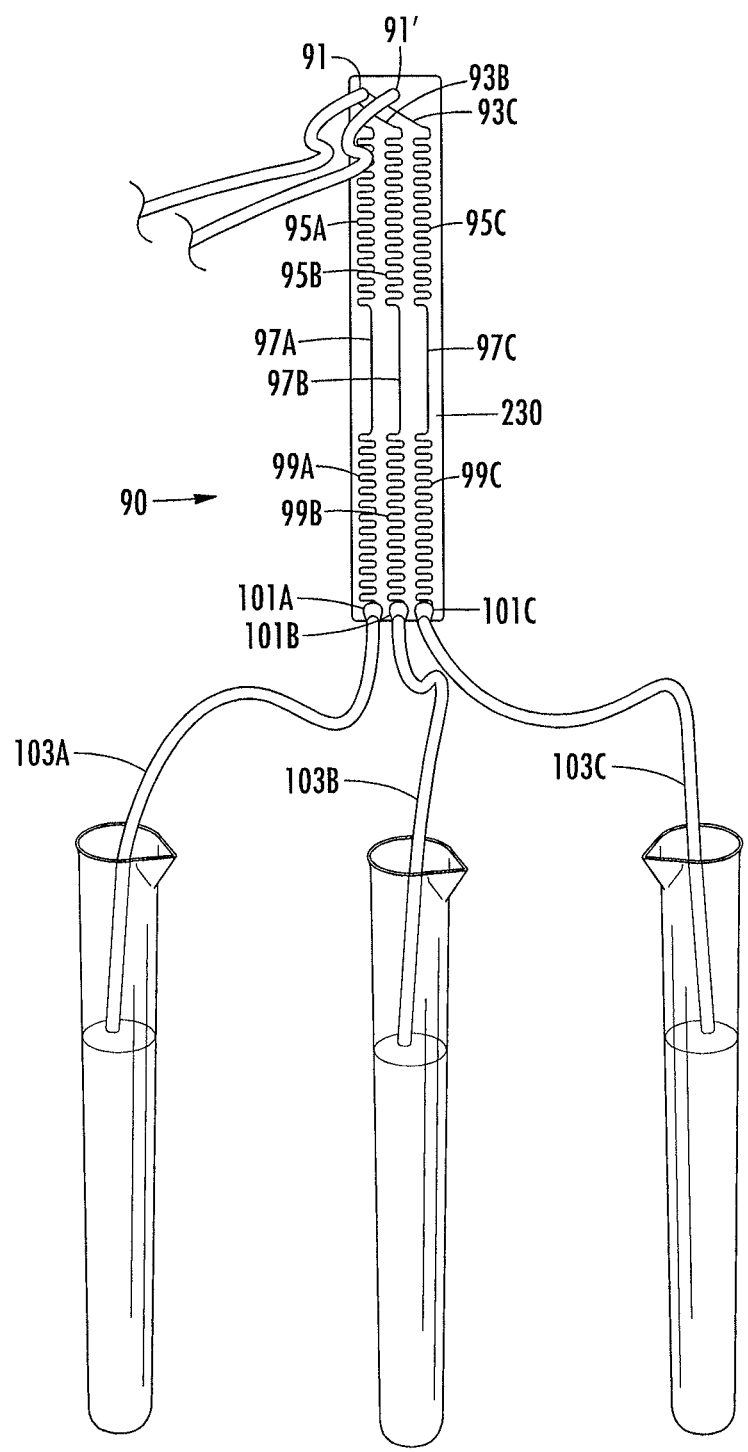
FIG. 12 is a front view of an embodiment of an apparatus for maintaining substantially even fluid flow in channels.

FIG. 12 illustrates an embodiment of an apparatus 90 for maintaining substantially even fluid flow in fluid pathways. The apparatus 90 preferably includes a housing 230 that supports a first set of fluid pathways, as well as a fluid input 91 and fluid output(s) 103A, 103B, 103C therefor. In a more preferred embodiment, the apparatus 90 also includes a housing 230' (FIG. 13) that supports a second set of fluid pathways, as well as a fluid input 91' and fluid output(s) (not shown) therefor. The housings 230, 230' can be any structure suitable to support the fluid pathways, inputs, and outputs.

Preferably, the housings 230, 230' support the fluid pathways such that fluid can be pumped to flow through the fluid pathways such that the system (and specifically the fluid flow) is unaffected by gravity.

C. Fluid Input(s)

Figure 13:
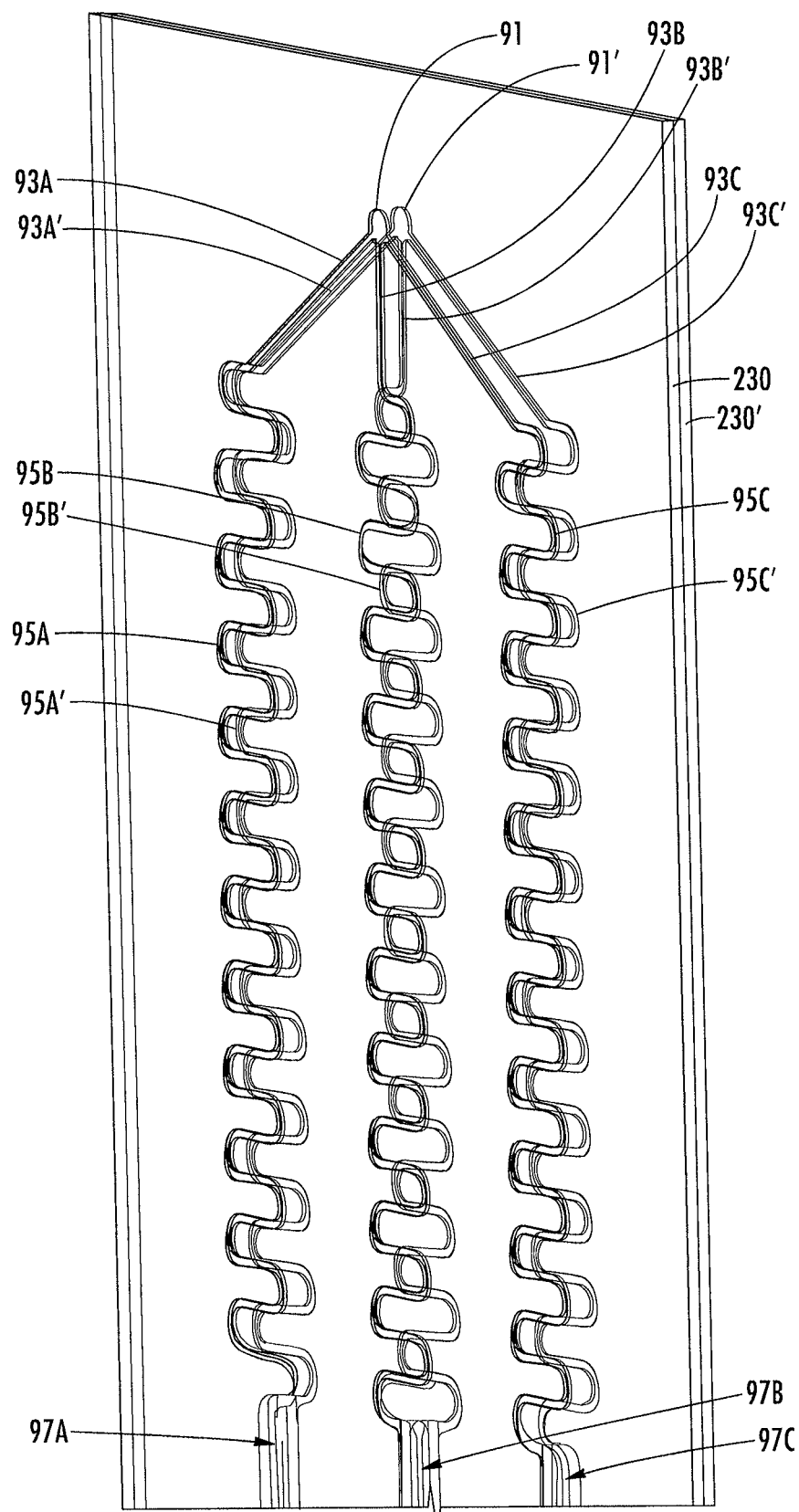
FIG. 13 is a perspective view of an embodiment of a portion of the apparatus shown in FIG. 12.

Apparatus 90 has fluid inputs 91 and 91' that are configured to receive fluid from external sources. Each of fluid inputs 91 and 91' can be configured, by conventional means, for connection with a respective fluid source (not shown) (e.g., an IV bag, etc.), such that fluid inputs 91 and 91' receive a first fluid and a second fluid, respectively, from the fluid sources. FIG. 13 shows a perspective view of apparatus 90 having the fluid input 91 configured to receive a first fluid and the fluid input 91' configured to receive a second fluid. Fluid inputs 91 and 91' are in fluid communication with the first and second set of fluid pathways, respectively.

D. First Set of Fluid Pathways

FIG. 12 shows the first set of fluid pathways. Though three fluid pathways are depicted, there could be more or less. Each fluid pathway preferably includes an input channel 93A, 93B, 93C, a first flow resistor portion 95A, 95B, 95C, a fluid channel 97A, 97B, 97C, a second flow resistor portion 99A, 99B, 99C, and an output channel 101A, 101B, and 101C. Each of the input channel 93A, 93B, 93C are in fluid communication with the fluid input 91 to receive the fluid from the fluid input 91. Each input channel 93A, 93B, 93C is in fluid communication with the corresponding first flow resistor portion 95A, 95B, 95C, which in turn is in fluid communication with the corresponding fluid channel 97A, 97B, 97C, which in turn is in fluid communication with the corresponding second flow resistor portion 99A, 99B, 99C, which in turn is in fluid communication with the corresponding output channel 101A, 101B, and 101C.

1. First Flow Resistor Portions

The first flow resistor portions 95A, 95B, 95C are configured to increase fluid resistance in the fluid pathways. In the illustrated embodiment, each of the first flow resistor portions 95A, 95B, 95C increases fluid resistance by changing the direction of the flow in the fluid pathway. For example, the first flow resistor portions 95A, 95B, 95C can have a serpentine shape, which changes the direction of fluid flow and increases a length of a fluid pathway. Preferably, each first flow resistor portion 95A, 95B, 95C is configured to avoid excessive shear rates in any turn or change of direction. Preferably, each first flow resistor portion 95A, 95B, 95C is configured to maintain shear rates less than 2000 inverse seconds ($s^{-1}$).

In some embodiments, the first flow resistor portions 95A, 95B, 95C can have an approximately square cross-sectional shape, but other appropriate cross-sectional shapes could be utilized. Preferably, each of the first flow resistor portions 95A, 95B, 95C has a width and a height in the range of 0.4 to 1.0 mm, and more preferably a width of about 0.8 mm and a height of about 0.75 mm high. However, other suitable dimensions could be used, as appropriate.

2. Fluid Channels

Figure 15:
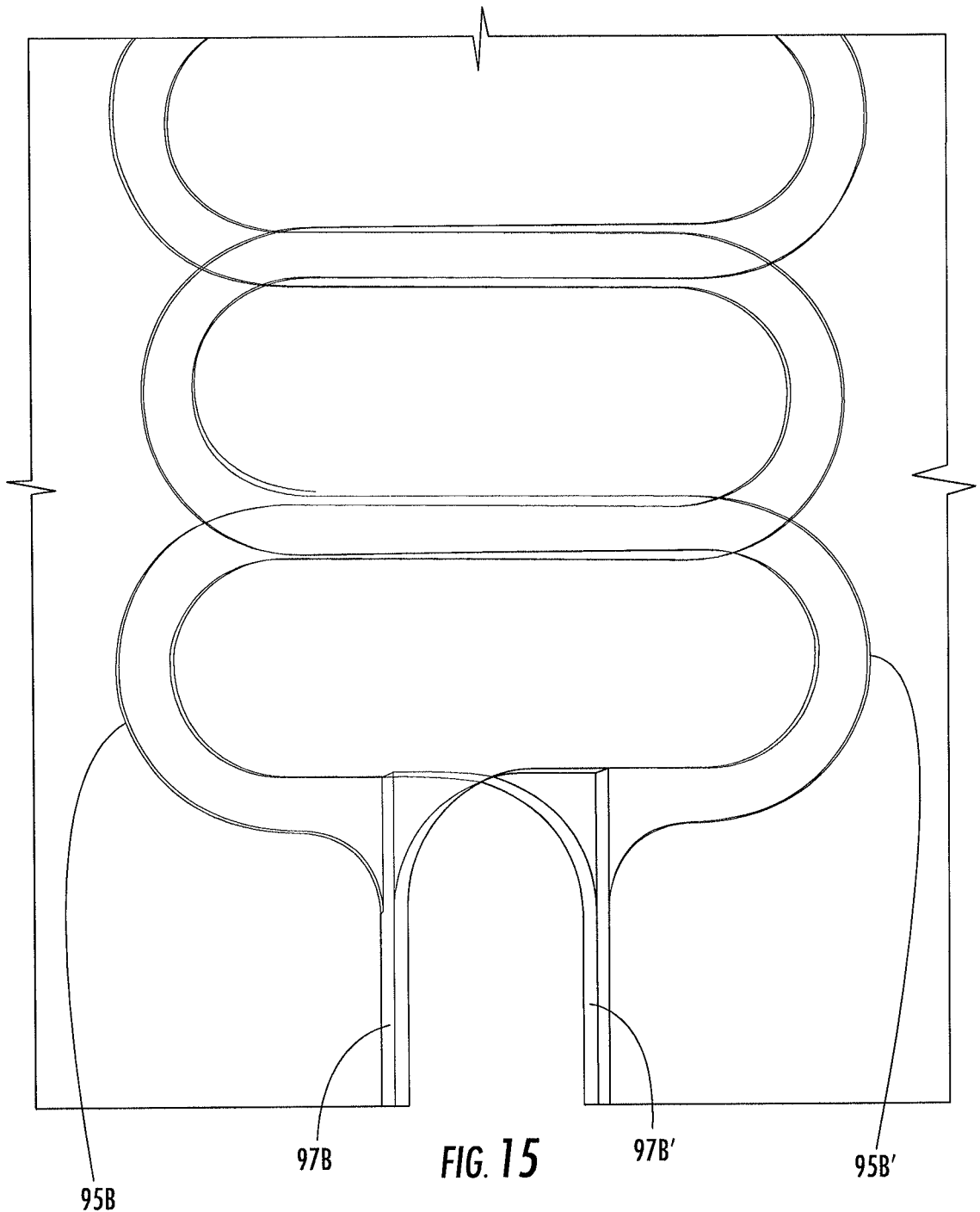
FIG. 15 is a front view of an embodiment of a connection of a first fluid resistor portion with a straight channel portion of the apparatus shown in FIG. 12.
Figure 16:
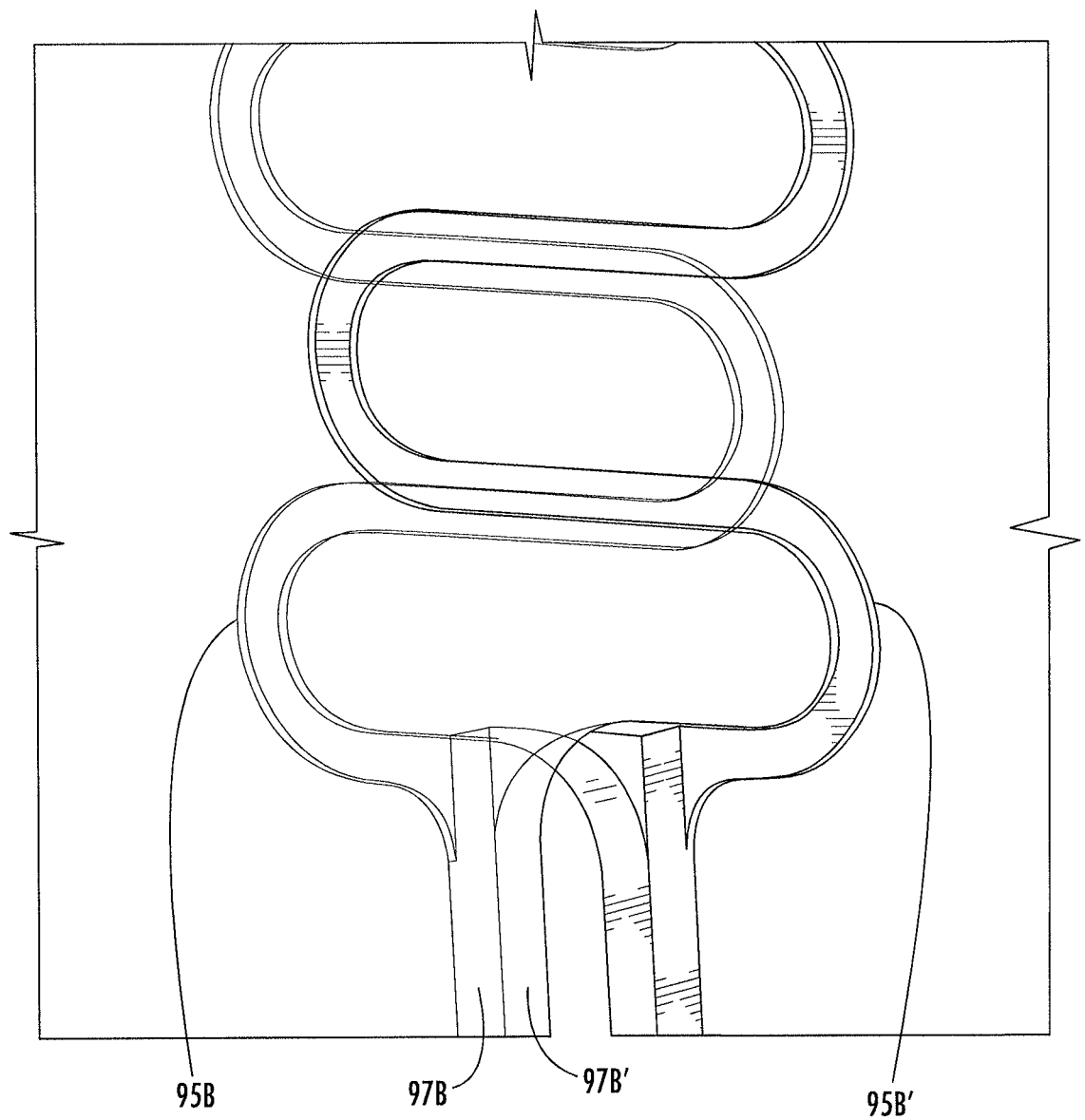
FIG. 16 is a perspective view of the connection of the first fluid resistor portion with the straight channel portion shown in FIG. 15.

Fluid channels 97A, 97B, 97C are in fluid communication with and positioned downstream to receive fluid from the first flow resistor portions 95A, 95B, 95C. FIGS. 15 and 16 show a portion of the central fluid pathway, in which the first flow resistor portion 95B supplies fluid into the fluid channel 97B. The fluid channels 97A, 97B, 97C each preferably extend substantially straight and in parallel to one another.

The fluid channels 97A, 97B, 97C each can be fully enclosed channels to contain fluid. However, in the illustrated embodiment (see FIGS. 15 and 16), the fluid channels 97A, 97B, 97C are open on one side to permit fluid communication with the fluid channels (only 97B is shown in FIGS. 15 and 16) of the second set of fluid pathways. In the illustrated embodiment, each fluid channel of the first set of fluid pathways and the corresponding fluid channel of the second set of fluid pathways can combine to form a fluid channel having the same configuration as the fluid channel 21 described above in regard to the first embodiment of an apparatus for flowing multiple fluids in a single channel. As another alternative, the fluid channels of the first and second sets of fluid pathways could be reconfigured and combined to form a fluid channel having the same configuration as the fluid channel 75 described above in regard to the second embodiment of an apparatus for flowing multiple fluids in a single channel.

3. Second Flow Resistor Portions

Figure 17:
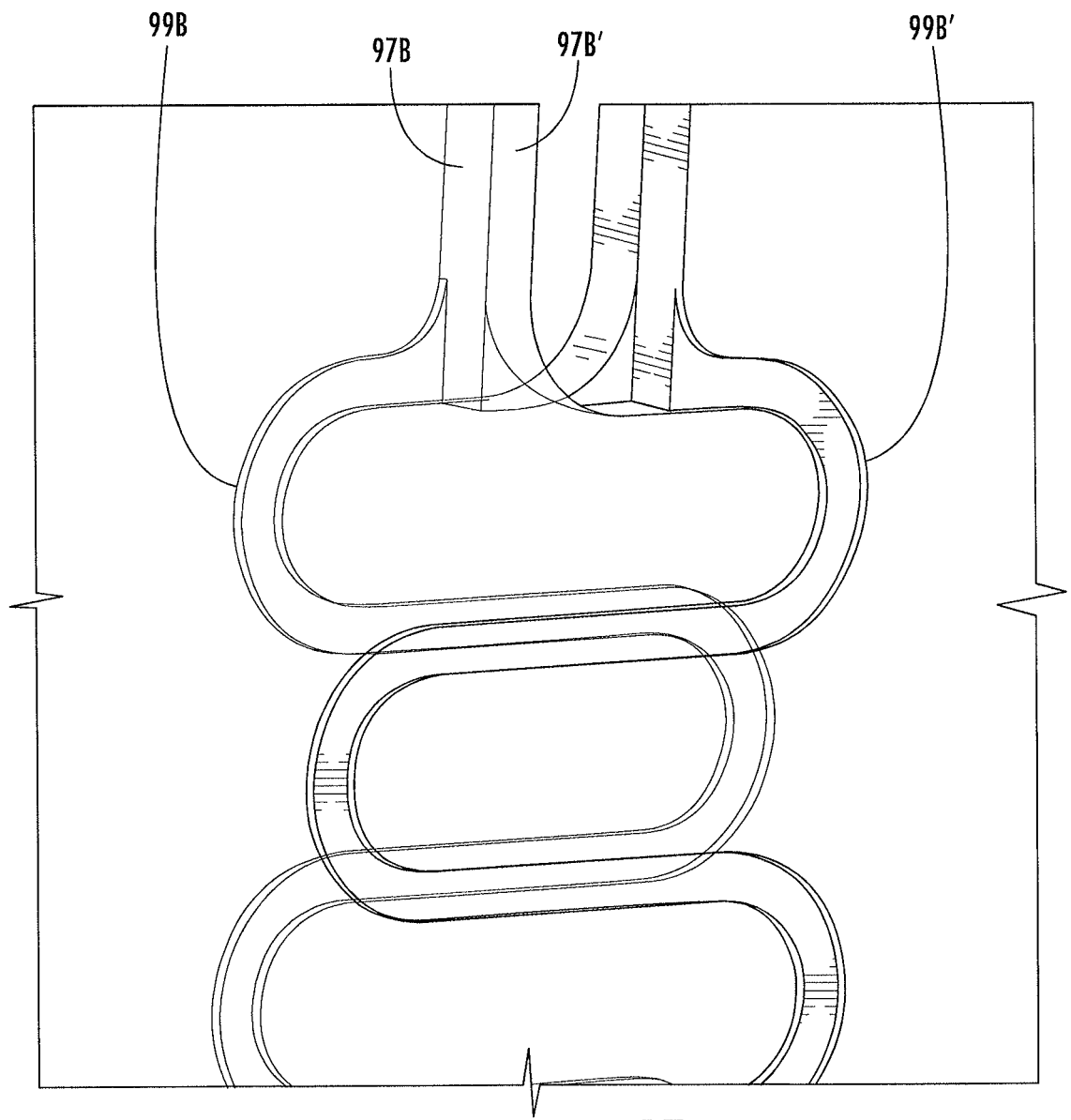
FIG. 17 is a perspective view of an embodiment of a connection of the straight channel portion and a second fluid resistor portion of the apparatus shown in FIG. 12.

The second flow resistor portions 99A, 99B, 99C are configured to increase fluid resistance in the fluid pathways. Preferably the second flow resistor portions 99A, 99B, 99C are in fluid communication with and positioned downstream to receive fluid from the fluid channels 97A, 97B, 97C. FIG. 17 shows a portion of the central fluid pathway, in which the second flow resistor portion 99B receives fluid from the fluid channel 97B. In the illustrated embodiment, each of the second flow resistor portions 99A, 99B, 99C increases fluid resistance by changing the direction of the flow in the fluid pathway. For example, the second flow resistor portions 99A, 99B, 99C can each have a serpentine shape, which changes the direction of fluid flow and increases a length of fluid pathway. For example, the combination of the first fluid flow resistor portions 95A, 95B, 95C and the second flow resistor portions 99A, 99B, 99C may increase the total length of the fluid pathway by 3 times what the total length would be if the first and second flow resistor portions were straight instead of being serpentine. Preferably, each first flow resistor portion 99A, 99B, 99C is configured to avoid excessive shear rates in any turn or change of direction. As a specific example, each second flow resistor portions 99A, 99B, 99C is configured to maintain shear rates less than 2000 inverse seconds ($s^{-1}$).

In some embodiments, the second flow resistor portions 99A, 99B, 99C can have an approximately square cross-sectional shape, but other appropriate cross-sectional shapes could be utilized. Preferably, each of the second flow resistor portions 99A, 99B, 99C has a width and a height in the range of 0.4 to 1.0 mm, and more preferably a width of about 0.8 mm and a height of about 0.75 mm high. However, other suitable dimensions could be used, as appropriate.

E. Fluid Output(s)

Apparatus 90 can have a single fluid output for each of the first and second set of fluid pathways. In a more preferred embodiment shown in FIG. 12, the first set of fluid pathways has a plurality of fluid outputs 103A, 103B, 103C, which allow fluid to exit a corresponding one of the first set of fluid pathways. The fluid outputs can be configured, by conventional means, to connect with further tubing or receptacles for the fluid. The second set of fluid pathways can have similar fluid output(s).

F. Second Set of Fluid Pathways

Figure 14:
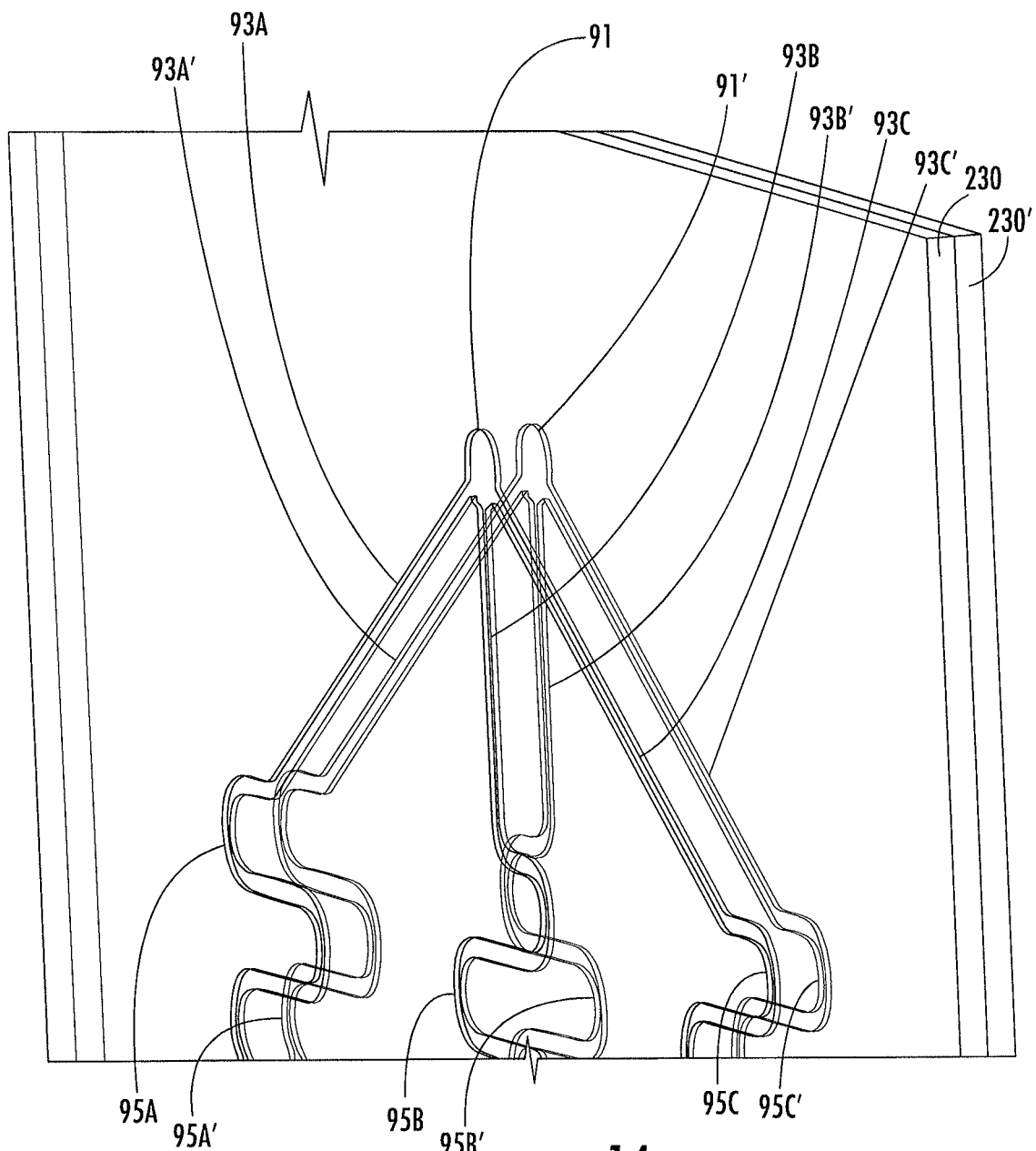
FIG. 14 is a perspective view of an embodiment of fluid inputs and fluid channels of the apparatus shown in FIG. 12.

FIGS. 13 and 14 show a portion of the second set of fluid pathways, which each preferably include an input channel 93A', 93B', 93C', a first flow resistor portion 95A', 95B', 95C', a fluid channel (only 97B' is shown in FIGS. 15, 16, and 17), a second flow resistor portion (only 99B' is shown in FIG. 17), and an output channel (not shown). The components of the second set of fluid pathways are essentially the same as the first set of fluid pathways, except that the second set of fluid pathways is supported on the housing 230'. The first and second sets of fluid pathways are not in fluid communication, except in certain embodiments within the respective fluid channels.

G. Configurations of Flow Resistor Portions

In the embodiments described above, a fluid pathway in the first set of fluid pathways and a corresponding fluid pathway in the second set of fluid pathways may have the same configuration, e.g., both of the corresponding fluid pathways will have the same configuration for the first flow resistor portion, fluid channel, and second flow resistor portion. However, it is contemplated that the corresponding fluid pathways may have different configurations, e.g., differences in the flow resistor portions, to achieve balanced and/or desired flow across corresponding fluid pathways. Some contemplated embodiments are more specifically described below.

Figure 18:
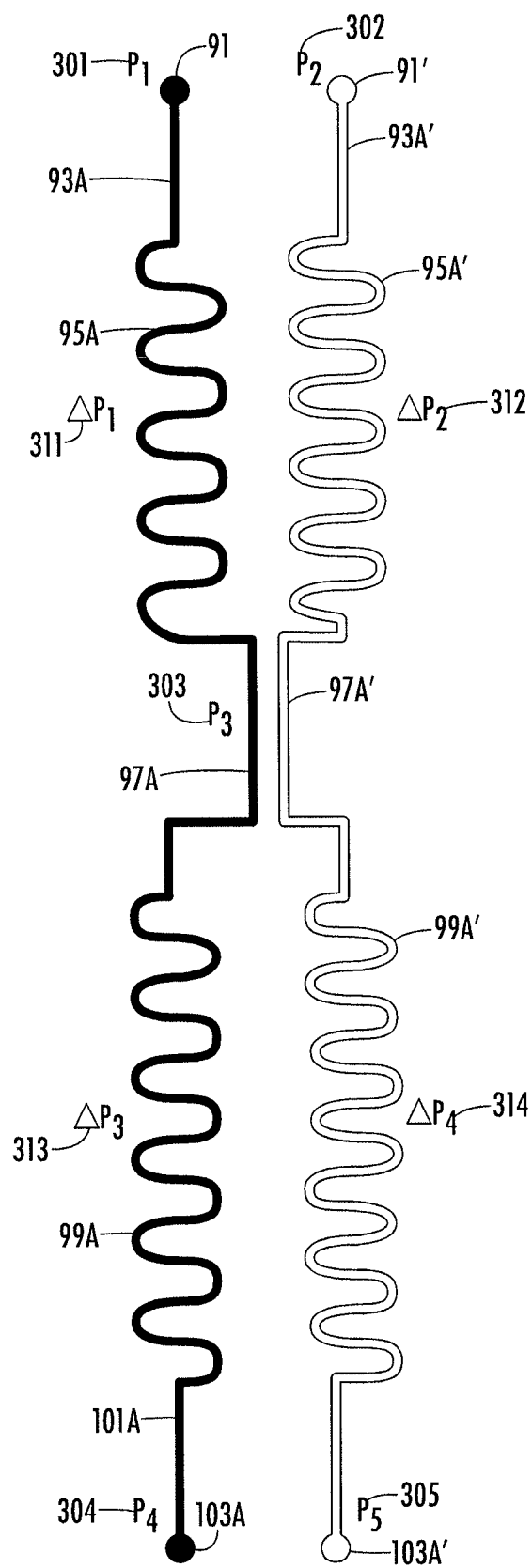
FIG. 18 is a schematic illustration of an embodiment of corresponding fluid pathways of the apparatus shown in FIG. 12.

For example, FIG. 18 shows an embodiment in which both of the corresponding fluid pathways of first and second sets of fluid pathways will have the same configuration for the first flow resistor portion, fluid channel, and second flow resistor portion. In particular, one fluid pathway of the first set of fluid pathways includes the fluid input 91 with an associated pressure 301 of $P_1$, an input channel 93A, a first flow resistor portion 95A with an associated pressure differential 311 of $\Delta P_1$, a fluid channel 97A with an associated pressure 303 of $P_3$, a second flow resistor portion 99A with an associated pressure differential 313 of $\Delta P_3$, an output channel 101A, and a fluid output 103A with an associated pressure 304 of $P_4$. The corresponding fluid pathway of the second set of fluid pathways includes a fluid input 91' with an associated pressure 302 of $P_2$, an input channel 93A', a first flow resistor portion 95A' with an associated pressure differential 312 of $\Delta P_2$, a fluid channel 97A' with an associated pressure 303 of $P_3$, a second flow resistor portion 99A' with an associated pressure differential 314 of $\Delta P_4$, an output channel 101A', and a fluid output 103A' with an associated pressure 305 of $P_5$. Because the first fluid and the second fluid are in fluid communication where fluid channels 97A and 97A' coincide, both the first fluid and the second fluid will have substantially the same pressure 303 of $P_3$ at the region of coincidence of the fluid channels 97A and 97A'. Such a configuration will provide desired operation if the first and second fluids have substantially the same viscosity.

However, if the second fluid is more viscous than the first fluid, that configuration may be less than optimal. For example, if the fluid output 103A is set at atmospheric pressure (that is, the fluid output 103A is open to the atmosphere), then the following relationship (14) holds:

$$P_4 = 0$$

and relationship (15):

$$P_3 = P_4 + \Delta P_3$$

and relationship (16):

$$P_5 = P_3 - \Delta P_4.$$

Substituting relationships (14) and (15) into relationship (16) yields relationship (17):

$$P_5 = P_4 + \Delta P_3 - \Delta P_4 - \Delta P_3 - \Delta P_4.$$

Because the second fluid is more viscous than the first fluid, then relationship (18) also holds:

$$\Delta P_4 > \Delta P_3.$$

Given relationship (18), then relationship (19) follows:

$$P_5 < 0,$$

thereby indicating that the fluid output 103A' of the fluid pathway of the second set of fluid pathways is in a vacuum. It is undesirable to have the fluid output 103A' in a vacuum because, particularly when each fluid pathway includes a flexible tubing, the tubing may pinch when subjected to a vacuum.

Figure 19:
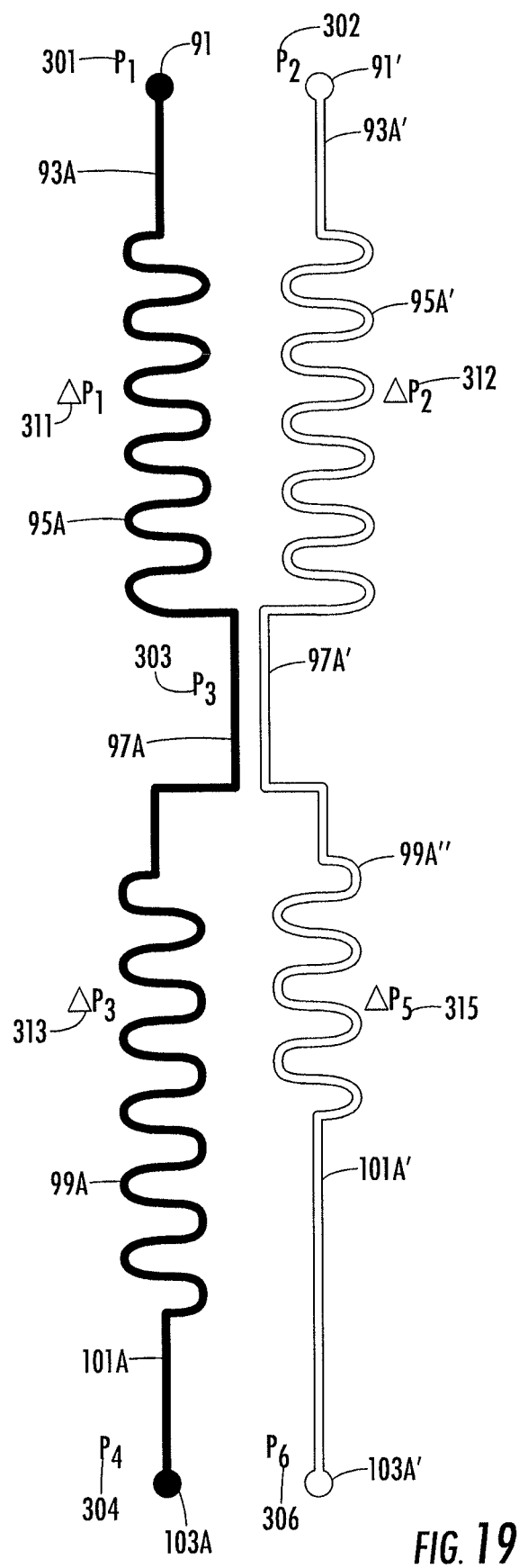
FIG. 19 is a schematic illustration of another embodiment of corresponding fluid pathways of the apparatus shown in FIG. 12.

To avoid the problems associated with having the fluid output 103A' under a vacuum, a smaller resistor portion may be used for the fluid pathway in which the second fluid flows. For example, as shown in FIG. 19, the fluid pathway of the second set of fluid pathways includes a second resistor portion 99A" rather than the second resistor portion 99A'. The second resistor portion 99A" has an associate pressure differential 315 of $\Delta P_5$ which is different than the pressure differential 314 of $\Delta P_4$ shown in FIG. 18. In this aspect, $\Delta P_5$ and $\Delta P_3$ may be set such that $\Delta P_5$ is equivalent to $\Delta P_3$ or such that the fluid output 103A' has a pressure 306 of $P_6$ that does not drop below zero.

Figure 20:
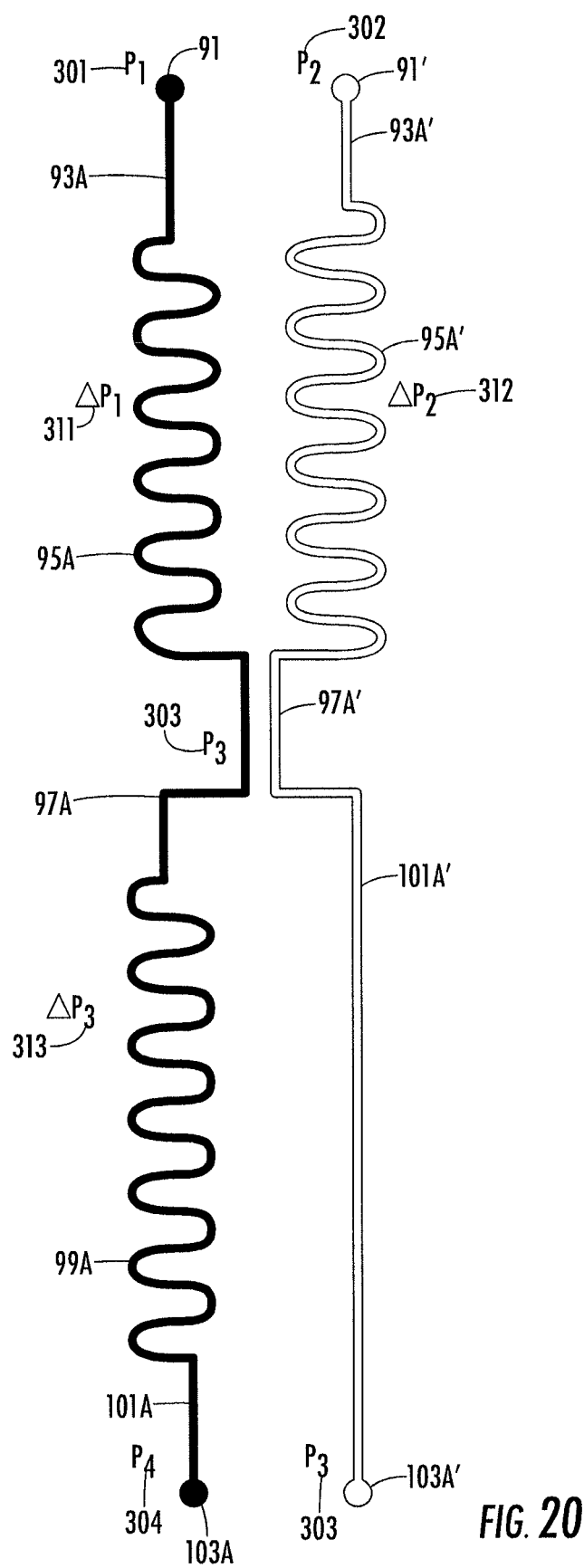
FIG. 20 is a schematic illustration of yet another embodiment of corresponding fluid pathways of the apparatus shown in FIG. 12.

Another alternative to avoiding the problems associated with having the fluid output 103A' under a vacuum, the fluid pathway in which the second fluid flows may omit the second flow resistor portion 99A' entirely. For example, as shown in FIG. 20, the fluid pathway of the second set of fluid pathways includes a fluid channel 97A' which is in direct fluid communication with the fluid pathway 101A', without an intermediate second flow resistor portion 99A' therebetween.

The construction and arrangement of the apparatuses and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. An apparatus for flowing multiple fluids in a single channel while substantially maintaining fluid separation, comprising:
    a fluid channel configured to receive a first fluid and a second fluid,
    wherein at least a portion of the fluid channel has a first internal surface portion and a second internal surface portion,
    wherein the first internal surface portion is configured to have an affinity to the first fluid and the second internal surface portion is configured to have an affinity to the second fluid, and the first internal surface portion and the second internal surface portion have different fluid affinities,
    wherein the at least a portion of the fluid channel, including the first internal surface portion and the second internal surface portion, is configured to maintain substantially stable flow of the first fluid and the second fluid within the at least a portion of the fluid channel; and
    wherein the fluid channel is configured to allow equal volumetric flow rates of the first fluid and the second fluid in the at least a portion of the fluid channel, and a relationship between a dynamic viscosity of the first fluid $u_1$ and a dynamic viscosity of the second fluid $u_2$ satisfies the condition of $u_1 < 2\, u_2$.

2. The apparatus according to claim 1, wherein the first internal surface portion is one of oleophobic and hydrophobic, and the second internal surface portion is the other of oleophobic and hydrophobic.

3. The apparatus according to claim 1, wherein the first internal surface portion is one of hydrophilic and hydrophobic, and the second internal surface portion is the other of hydrophilic and hydrophobic.

4. The apparatus according to claim 1, further comprising:
    a first coating applied to at least a portion of the fluid channel to provide the first internal surface portion; and
    a second coating applied to at least a portion of the fluid channel to provide the second internal surface portion.

5. The apparatus according to claim 1, wherein the at least a portion of the fluid channel has a width w and a height h, and a ratio of the width w and the height h is within a range of 1:2 to 10:1.

6. The apparatus according to claim 5, the ratio of the width w and the height h is substantially 2:1.

7. An apparatus for flowing multiple fluids in a single channel while substantially maintaining fluid separation, comprising:
    a fluid channel comprising:
        a first fluid channel portion configured to receive a first fluid;
        a second fluid channel portion configured to wrap helically around the first fluid channel portion and configured to receive a second fluid; and
        an opening configured to allow for fluid contact between the first fluid flowing through the first fluid channel portion and the second fluid flowing through the second fluid channel portion.

8. The apparatus according to claim 7, wherein the fluid channel is configured to maintain substantially stable flow of the first fluid and the second fluid within the fluid channel.

9. The apparatus according to claim 7, wherein the first fluid channel portion is substantially straight.

10. The apparatus according to claim 7, wherein the first fluid channel portion and the second fluid channel portion each have a substantially circular cross-section.

* * * * *